United States Patent [19]
Fields et al.

[11] Patent Number: 6,019,749
[45] Date of Patent: Feb. 1, 2000

[54] APPARATUS AND METHOD FOR REMOVING MATERIAL FROM SKIN PORES

[75] Inventors: Kathy A. Fields, San Francisco; Leonard L. Hofheins, Walnut Creek; Katheryn P. Rodan, Piedmont; Del M. Thornock, Concord, all of Calif.

[73] Assignee: Squeezease, LLC, Piedmont, Calif.

[21] Appl. No.: 09/053,558

[22] Filed: Apr. 1, 1998

[51] Int. Cl.[7] .................................................. A61M 1/00
[52] U.S. Cl. .......................... 604/313; 604/315; 604/289; 604/40
[58] Field of Search .................................. 604/289, 310, 604/311, 312, 313, 315, 316, 35, 36, 39, 40, 94; 600/578; 606/201; 15/415.1, 341

[56] References Cited

U.S. PATENT DOCUMENTS

| | | |
|---|---|---|
| D. 279,405 | 6/1985 | Lentz . |
| D. 322,483 | 12/1991 | Kishimoto . |
| 1,570,370 | 1/1926 | Brodersen et al. ...................... 604/316 |
| 2,076,410 | 4/1937 | McGerry .................................. 604/313 |
| 2,267,636 | 12/1941 | Benton ..................................... 604/315 |
| 2,308,837 | 1/1943 | Smith ....................................... 604/315 |
| 2,612,892 | 10/1952 | Beatman ................................. 604/313 |
| 2,631,583 | 3/1953 | Levergne ................................. 604/312 |
| 3,763,854 | 10/1973 | Welch ...................................... 604/313 |
| 3,794,035 | 2/1974 | Brenner ................................... 604/313 |
| 3,896,810 | 7/1975 | Akiyama . |
| 4,151,832 | 5/1979 | Hamer ..................................... 128/765 |
| 4,182,329 | 1/1980 | Smit et al. . |
| 4,195,440 | 4/1980 | Rodrigue . |
| 4,292,971 | 10/1981 | Smit et al. . |
| 4,692,140 | 9/1987 | Olson ........................................ 604/40 |
| 4,701,167 | 10/1987 | Chekan .................................... 604/310 |
| 4,900,316 | 2/1990 | Yamamoto .............................. 604/313 |
| 5,098,414 | 3/1992 | Walker ..................................... 604/291 |
| 5,187,833 | 2/1993 | Bieganski . |
| 5,280,668 | 1/1994 | Fortune . |
| 5,295,956 | 3/1994 | Bales et al. ............................... 604/30 |
| 5,295,982 | 3/1994 | Schatz . |
| 5,377,895 | 1/1995 | Masreliez . |
| 5,387,203 | 2/1995 | Goodrich . |
| 5,549,584 | 8/1996 | Gross . |
| 5,624,416 | 4/1997 | Schatz . |
| 5,662,677 | 9/1997 | Wimmer . |

*Primary Examiner*—Corrine McDermott
*Assistant Examiner*—David J. Cho
*Attorney, Agent, or Firm*—Thomas R. Lampe

[57] ABSTRACT

An apparatus and method for extracting matter from skin pores. The system utilizes a nozzle including relatively movable inner and outer nozzle portions. Vacuum is applied to the nozzle and the inner nozzle is applied to the skin surrounding a pore after the skin has been drawn into the outer nozzle portion by vacuum.

14 Claims, 8 Drawing Sheets

APPARATUS AND METHOD FOR REMOVING MATERIAL FROM SKIN PORES

TECHNICAL FIELD

This invention relates to an apparatus and method for cleaning the skin. More particularly, the system of the invention removes undesirable materials from skin pores. Such materials include sebum, dirt and bacteria, so called white and black comedones, which can cause pimples, commonly known as zits, and other skin blemishes.

BACKGROUND OF THE INVENTION

The apparatus of the present invention utilizes vacuum during the process of removing material from skin pores. The use of vacuum per se is known for such purpose. However, prior art so-called comedone extractors often require use by trained and skilled personnel and the processes employed can be time consuming. Extractors for home use also exist, but reliability and/or complexity are problems.

U.S. Pat. No. 5,624,416, issued Apr. 29, 1997, discloses a device for cleaning skin pores which incorporates a suction nozzle with several openings. The skin is drawn by a pulsating suction force into the openings and spaced movable jaws are employed which press against the skin and squeeze contaminants from the skin pore so that the pulsed suction can withdraw them. It will be appreciated that such a system requires synchronization between the pulsating suction force and the pulsating compression force of the jaws.

Other devices employing suction devices for cleaning skin are shown, for example, in U.S. Pat. No. 5,295,982, issued Mar. 22, 1994, U.S. Pat. No. 4,292,971, issued Oct. 6, 1981, U.S. Pat. No. 4,182,329, issued Jan. 8, 1980, and U.S. Pat. No. DES. 322,483, issued Dec. 17, 1991.

Apparatus employing vacuum to extract other types of materials from a human body or objects are disclosed in U.S. Pat. No. 5,549,584, issued Aug. 27, 1996, U.S. Pat. No. 4,195,440, issued Apr. 1, 1980, U.S. Pat. No. 5,662,677, issued Sep. 2, 1997, U.S. Pat. No. 3,896,810, issued Jul. 29, 1975, U.S. Pat. No. 5,387,203, issued Feb. 7, 1995, U.S. Pat. No. 5,5,377,895, issued Jan. 3, 1995, U.S. Pat. No. 5,280,668, issued Jan. 25, 1994, and U.S. Pat. No. 5,187,833, issued Feb. 23, 1993.

The design of a mechanical comedone extractor is disclosed in U.S. Pat. No. DES. 279,405, issued Jun. 25, 1985.

DISCLOSURE OF INVENTION

The present invention relates to an apparatus and method for removing material from skin pores. The apparatus is relatively simple and inexpensive, as compared to conventional prior art devices, and the system can be efficiently and effectively employed by even an untrained individual to clean skin pores.

The apparatus includes a nozzle for engaging the skin of an individual, the nozzle including an outer nozzle portion having a outer nozzle portion distal end defining an outer nozzle portion opening and an inner nozzle portion having an inner nozzle portion distal end defining an inner nozzle portion opening.

The outer nozzle portion is movably mounted relative to the inner nozzle portion and movable between a first position wherein the inner nozzle portion distal end is spaced from and out of contact with skin engaged by the outer nozzle portion distal end and a second position wherein the outer nozzle portion is retracted relative to the inner nozzle portion and the inner nozzle portion distal end is in contact with skin engaged by the nozzle.

The apparatus also includes biasing means biasing the outer nozzle portion to the first position.

Vacuum producing means is employed for producing a vacuum at the nozzle for applying a vacuum to the skin for removing material from a pore of the skin.

The method of cleaning a skin pore of the present invention includes the step of bringing the distal end of a first nozzle portion into engagement with skin surrounding a pore to form a first annular seal between the skin and the distal end of the first nozzle portion surrounding the pore.

A vacuum is applied to the skin within the confines of the first annular seal formed between the skin and the first nozzle portion to deform the skin and draw the skin into the distal end of the first nozzle portion.

While the skin is deformed and drawn into the distal end of the first nozzle portion, the distal end of a second nozzle portion is brought into engagement with the deformed skin within the distal end of the first nozzle portion to form a second annular seal around the pore within the confines of the first annular seal.

A vacuum is applied to the skin within the confines of the second annular seal formed between the skin and the distal end of the second nozzle portion to extract material from the pore into the second nozzle portion.

Other features, advantages, and objects of the present invention will become apparent with reference to the following description and accompanying drawings.

MODES FOR CARRYING OUT THE INVENTION

Figure 1:
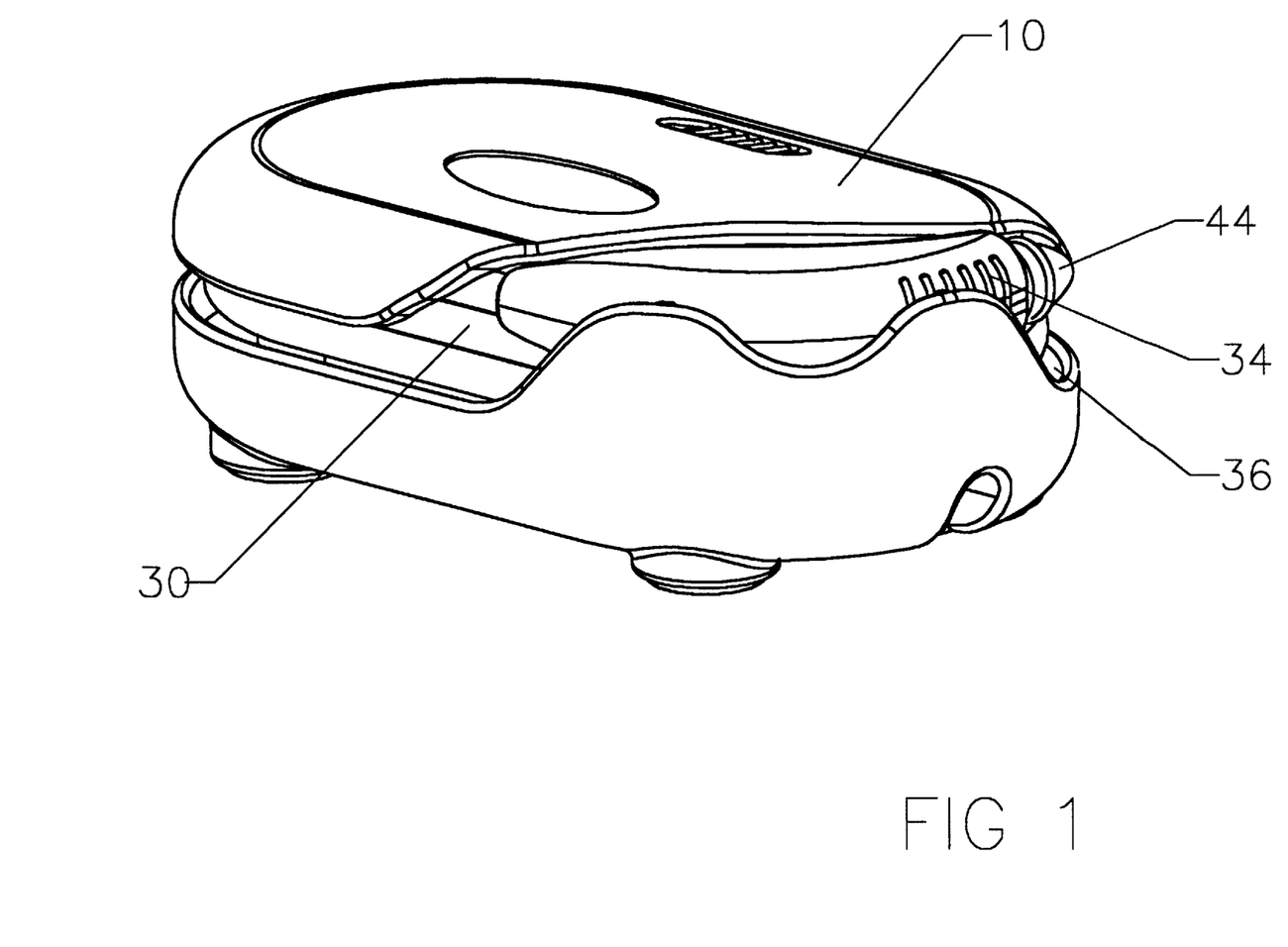
FIG. 1 is a perspective view of apparatus constructed in accordance with the teachings of the present invention.
Figure 2:
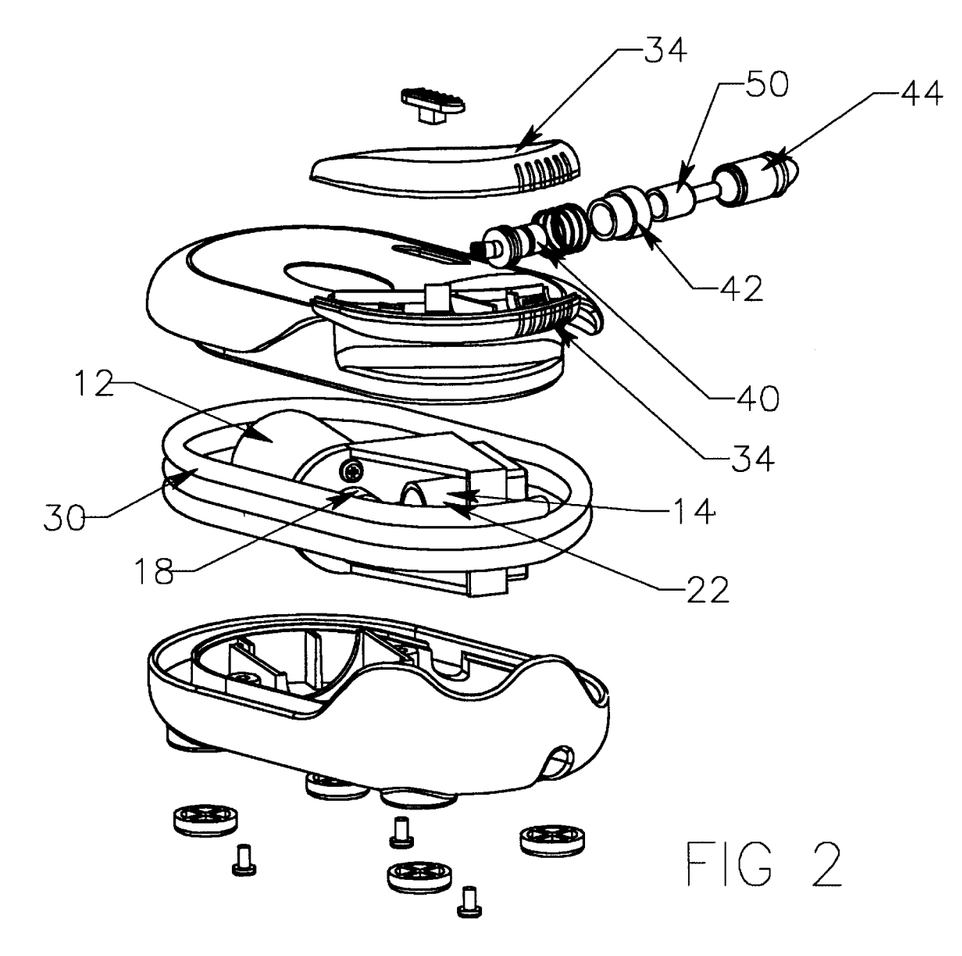
FIG. 2 is an exploded perspective view illustrating apparatus components.
Figure 3:
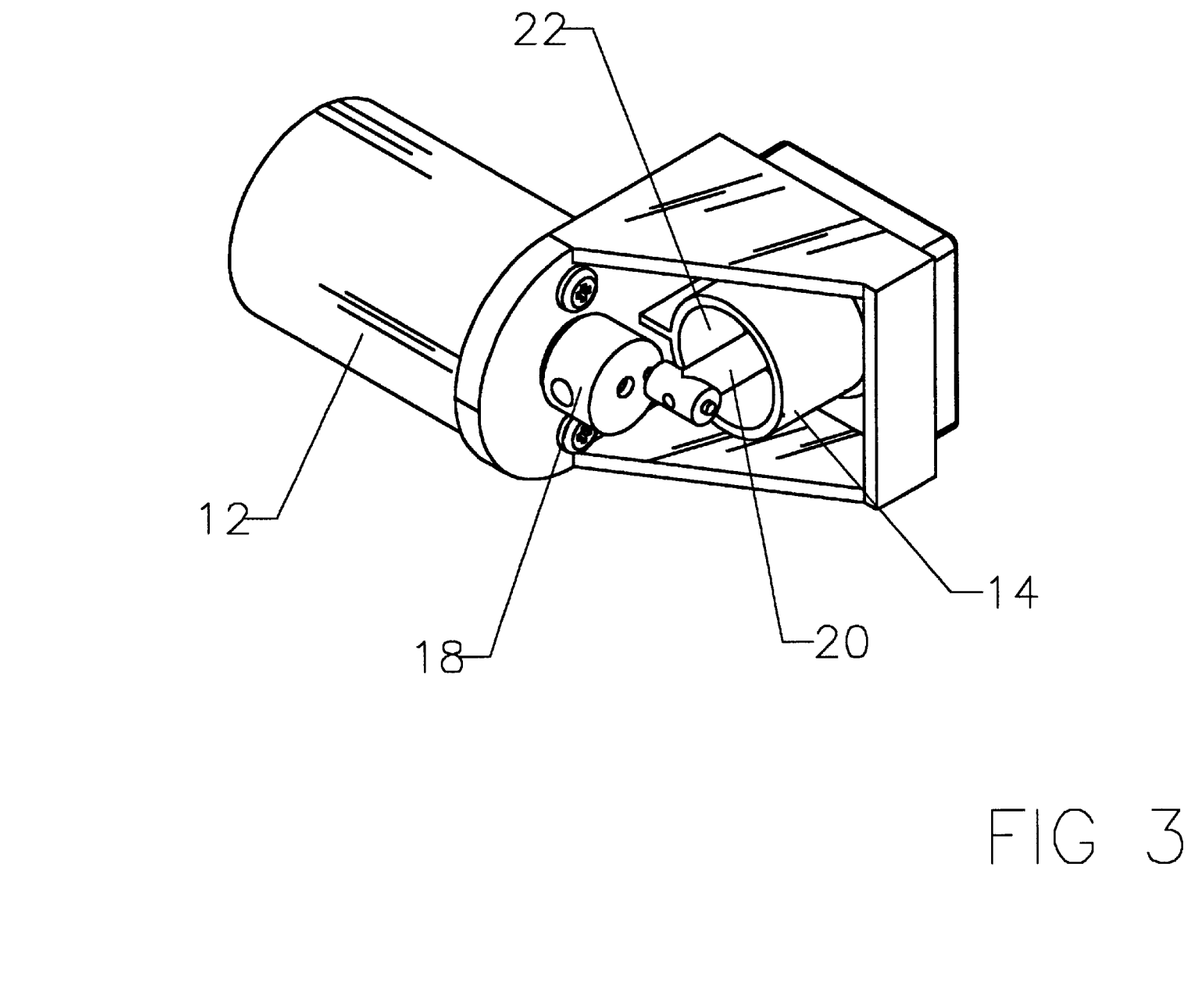
FIG. 3 is an enlarged perspective view of selective components of the apparatus, including a vacuum pump and motor.
Figure 4:
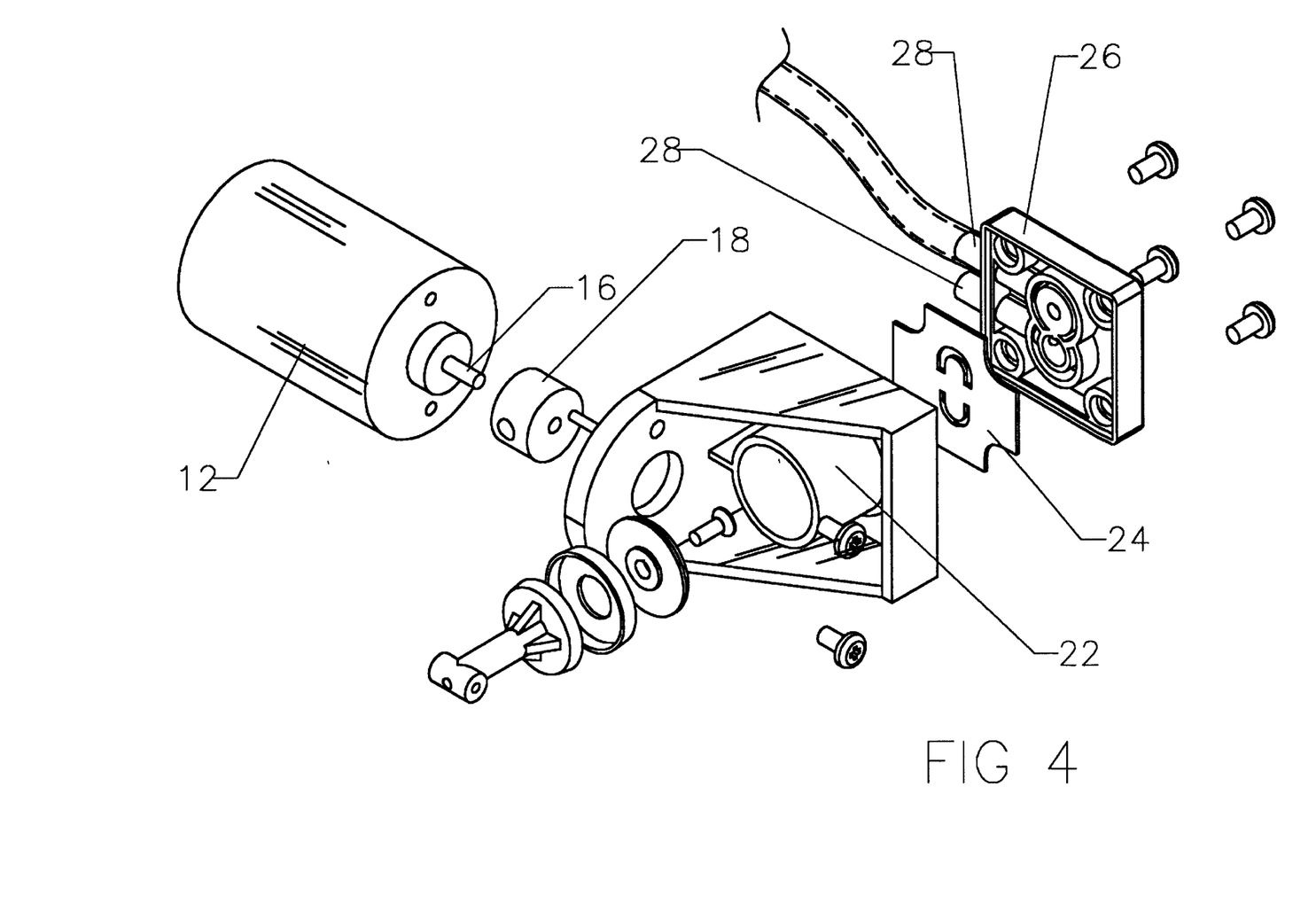
FIG. 4 is an exploded perspective view of the vacuum pump and motor.

Referring now to FIGS. 1–9, apparatus constructed in accordance with the teachings of the present invention includes a cabinet 10 accommodating therein a number of structural elements of the apparatus. More particularly, as shown in FIG. 2, the interior of the cabinet accommodates an electric motor 12 and a vacuum pump 14 driven by the electric motor. Details of the vacuum pump are also illustrated in FIGS. 3 and 4.

During operation of the electric motor and pump the spindle 16 of the motor drives an eccentric connector 18, the latter in turn causing reciprocation of pump piston 20 within pump cylinder 22. A flap valve 24 is disposed between the pump cylinder 22 and a valve element 26 having seats for the two flaps of the flap valve. Air flow conduits 28 lead from the valve element 26, one such conduit being an intake conduit and the other being an air outlet conduit. This structure need not be described in detail since vacuum pumps and valve combinations of this type are well known generally and the particular type of vacuum producing means employed in the invention apparatus is not at all critical.

Connected to the conduit 28 having a vacuum therein is a flexible hose or conduit 30. In the interest of clarity, hose 30 has not been shown in FIG. 2.

The end of the hose remote from valve element 26 leads to a manually graspable housing 34. When the apparatus is not in use, housing 34 may be accommodated in a recess 36 (FIG. 1) formed by cabinet 10. Similarly, the flexible hose 30 may be wrapped about the cabinet and reside in a suitable recess formed thereby to provide a neat, compact package.

Hose 30 is connected to a fitting 40 mounted within manually graspable housing 34. Slidably mounted on fitting 40 is a sleeve 42 which is enlarged at one end thereof to receive an outer nozzle portion 44. A coil compression spring 46 engages sleeve 42 and a rib element 48 within housing 34, the spring continuously biasing outer nozzle portion 44 outwardly, that is to the position illustrated in FIG. 5, for example. Outer nozzle portion 44 is suitably friction fit into sleeve 42 to retain the connection therebetween; however, the outer nozzle portion 44 may be removed from the sleeve for cleaning or other purposes by applying a pulling force of sufficient magnitude to the outer nozzle portion.

Located within the confines of outer nozzle portion 44 is an inner nozzle portion 50. Together, nozzle portions 44 and 50 form a nozzle. At the inner end thereof, i.e. the right end thereof as viewed from FIG. 5, for example, the inner nozzle portion 50 is enlarged and receives an end of fitting 40. A friction fit exists between the fitting 40 and the inner nozzle portion to releasably retain the inner nozzle portion in position.

Figure 5:
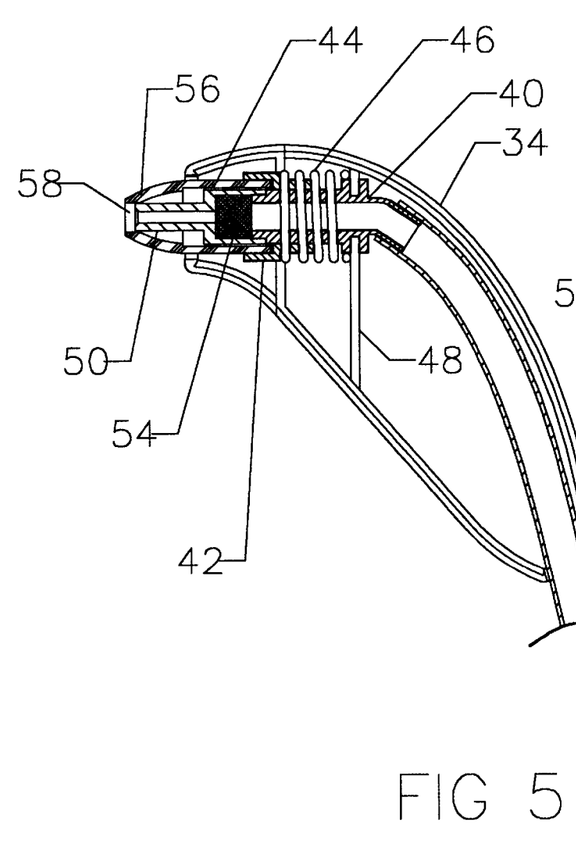
FIGS. 5 and 6 are enlarged partial cross-sectional views illustrating details of a hand held housing employed in the apparatus and the nozzle structure of the apparatus, components of the nozzle structure being illustrated in alternate positions.
Figure 6:
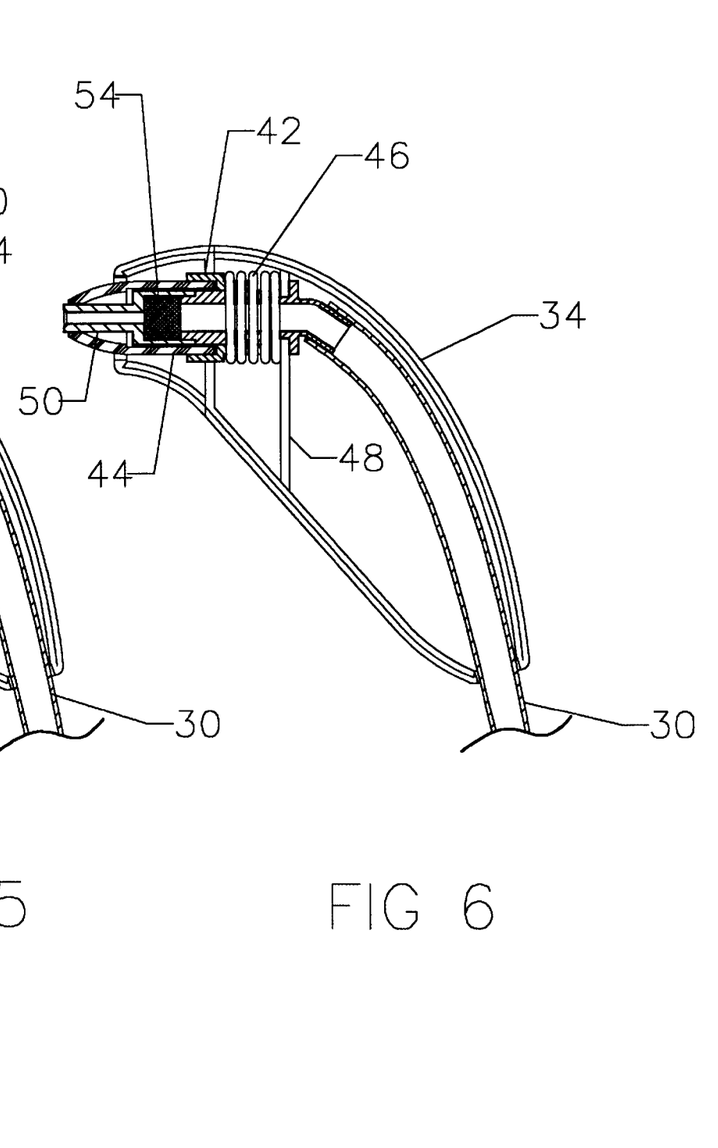

A filter 54 constructed of any suitable filter material is housed within the enlarged end of inner nozzle portion 50 and bears against an end of fitting 40. After outer nozzle portion 44 has been removed as described above, manual access may be had to inner nozzle portion 50 to remove same for replacement, cleaning or other purposes. The filter 54 is also exposed for ready removal and replacement along with inner nozzle portion 50.

Outer nozzle portion 44 has an outer nozzle portion distal end 56 defining an outer nozzle portion opening 58. Inner nozzle portion 50 has an inner nozzle portion distal end 60 defining an inner nozzle portion opening 62.

When the outer nozzle portion 44 is in the normal biased position shown in FIG. 5, for example, the inner nozzle portion distal end 60 is spaced from and out of contact with any skin engaged by the outer nozzle portion distal end. When, however, the outer nozzle portion is retracted relative to the inner nozzle portion to the position shown in FIG. 6, for example, the inner nozzle portion distal end will be in contact with skin engaged by the nozzle.

Figure 8:
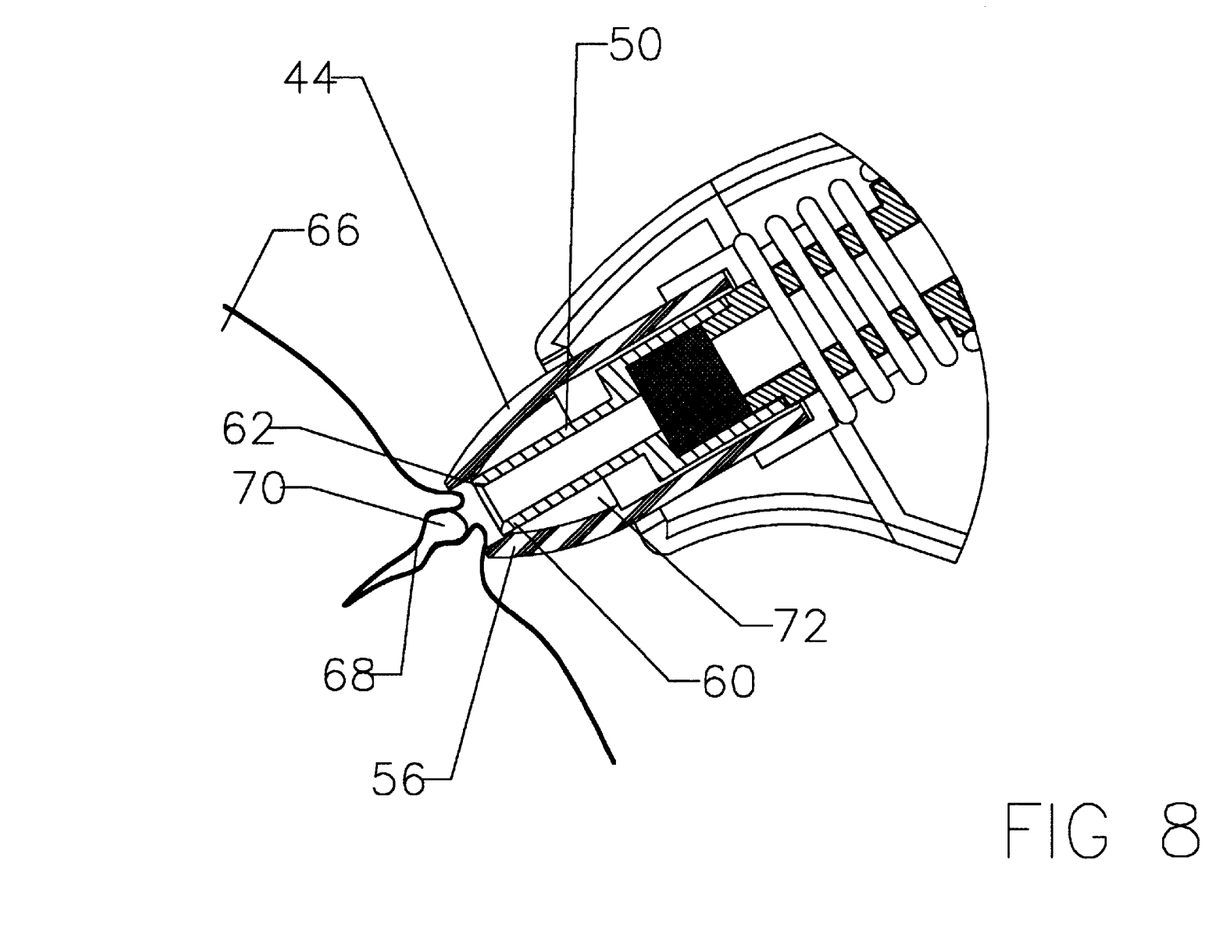
FIG. 8 is a greatly enlarged, cross-sectional, diagrammatic side view illustrating in schematic fashion a segment of the apparatus nozzle engaging human skin surrounding a pore having matter therein to be extracted.
Figure 9:
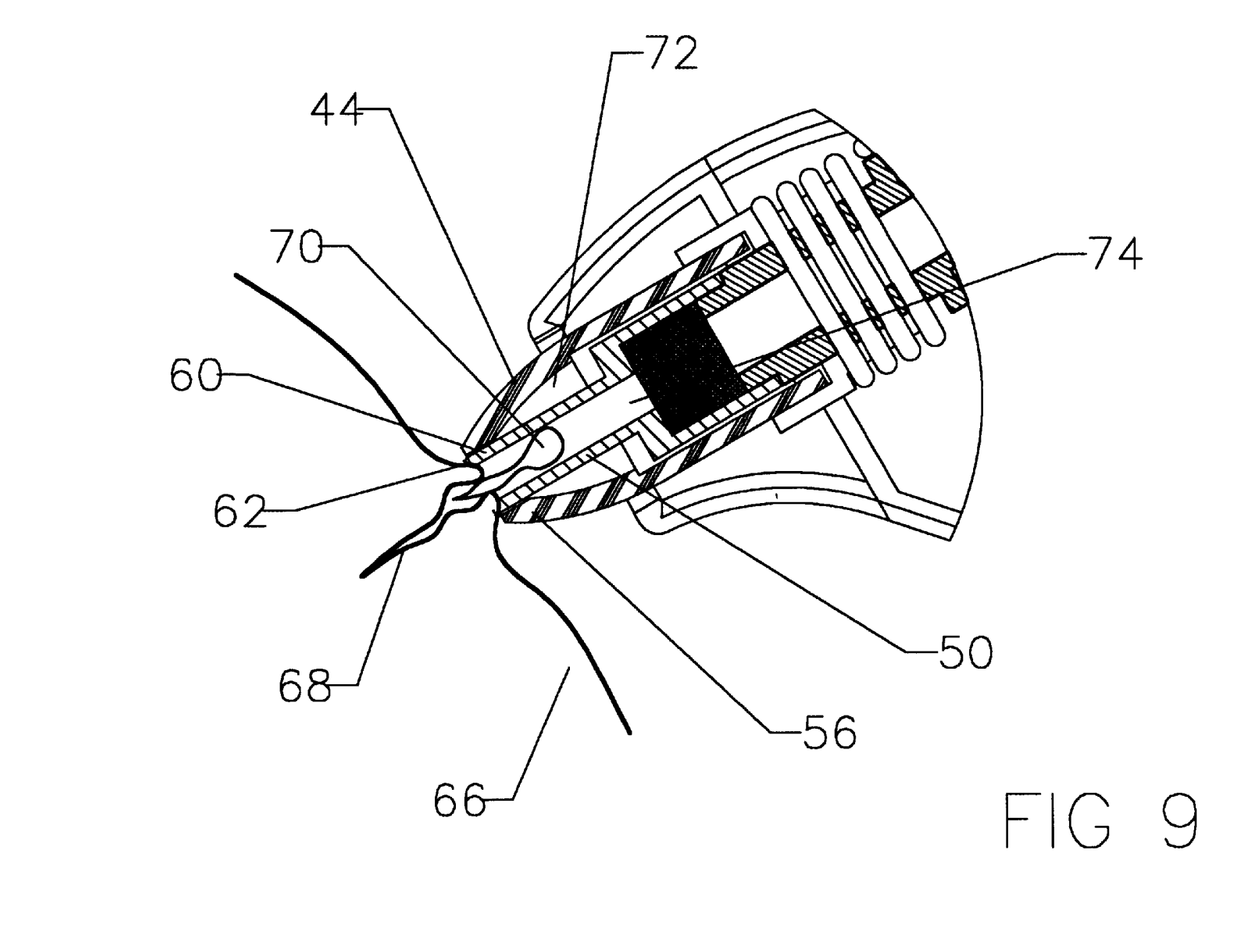
FIG. 9 is a view similar to FIG. 8 but showing the relative positions assumed by components of the nozzle during a latter stage of the extraction process with matter being removed by the apparatus from the skin pore.

FIGS. 8 and 9 show the nozzle comprised of the two nozzle portions in engagement with skin 66 around a pore 68 having material 70 therein.

FIG. 8 shows the initial positioning of the nozzle relative to the skin and pore to initiate the material extraction or cleaning process. It is to be understood that the electric motor 12 and vacuum pump 14 are being operated so that a vacuum is being applied to inner nozzle interior 74. This also creates a vacuum at outer nozzle portion opening 58. A suitable vacuum may for example, be within the range of 500 mm-600 mm mercury.

The distal end of the outer nozzle portion forms an annular seal between the skin and the distal end. The vacuum created at opening 58 within the confines of the annular seal causes the skin to deform and to be drawn into the distal end of the outer nozzle portion. This is shown in FIG. 8.

Now the person applying the apparatus pushes the manually graspable housing 34 and nozzle against the skin with greater force. This causes the outer nozzle portion to be retracted relative to the inner nozzle portion to assume the position shown in FIGS. 6 and 9. The distal end of the inner nozzle portion is generally centered relative to pore 68, surrounding the pore, and the matter 70 is pulled upwardly into interior 74 through inner nozzle portion opening 62 with the material 70 being collected at filter 54.

It will thus be seen that the extraction process is essentially a two stage operation, the first stage deforming the skin at the pore site to distort the skin and open the pore for the second stage of the extraction process which is the actual removal of the material from the pore. This is accomplished very quickly and efficiently. The annular seal created between the distal end of the inner nozzle portion is very localized with respect to the pore, being within the confines of the seal created between the outer nozzle portion and the skin.

Figures 7, 10, 11:
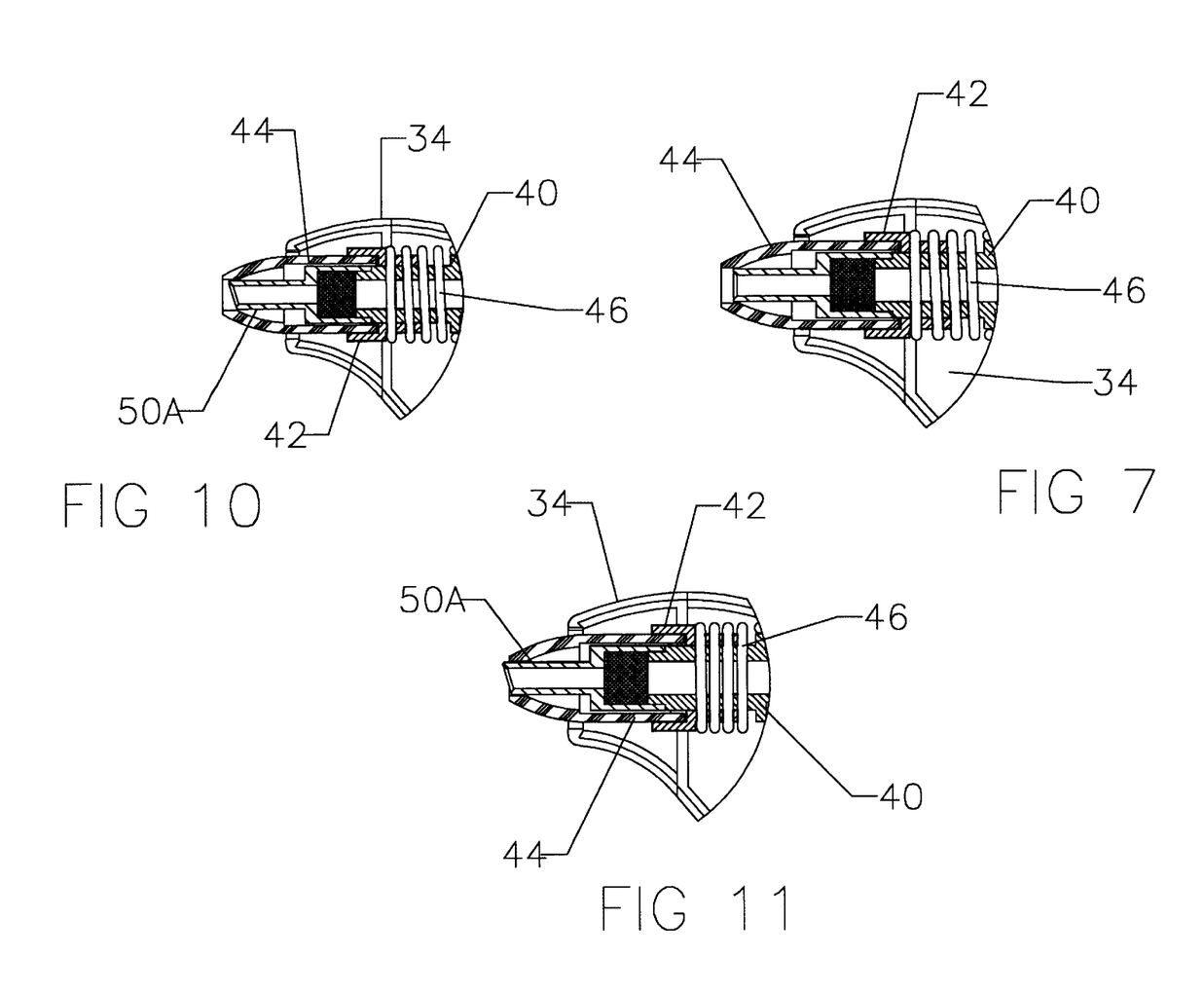
FIG. 7 is an enlarged cross-sectional side view of the apparatus nozzle and related structure.
FIGS. 10 and 11 are cross-sectional side views illustrating an alternative form of inner nozzle portion and the relative positions assumed by nozzle structural components during different stages of operation of the apparatus.

It will be noted that the distal end 60 of the inner nozzle portion 50 is tapered inwardly in the direction of air flow (shown by the arrows in FIGS. 8 and 9). Thus, a truncated cone-like cavity is created at the distal end. This configuration has been found to be highly effective for removing material from pores. However, other configurations may be employed. For example, FIGS. 10 and 11 illustrate an inner nozzle portion 50A having a distal end cut or formed at a bias. Also, different diameter openings and passageways may be utilized.

We claim:

1. An apparatus for removing material from a skin pore, said apparatus comprising, in combination:

a nozzle for engaging the skin of an individual, said nozzle including an outer nozzle portion defining an outer nozzle portion interior and having an outer nozzle portion distal end defining an outer nozzle portion opening communicating with said outer nozzle portion interior and an inner nozzle portion defining an inner nozzle portion interior and having an inner nozzle portion distal end defining an inner nozzle portion opening communicating with said inner nozzle portion interior, said outer nozzle portion and said inner nozzle portion being relatively movable whereby said inner nozzle portion distal end either is spaced from and out of contact with skin engaged by said outer nozzle portion distal end or is in contact with skin engaged by said outer nozzle distal end;

biasing means biasing one of said nozzle portions against movement relative to the other of said nozzle portions; and vacuum producing means for producing a vacuum at said nozzle within both said outer nozzle portion interior and said inner nozzle portion interior for applying a vacuum to skin engaged by said outer nozzle portion and said inner nozzle portion of said nozzle for removing material from a pore of said skin.

2. The apparatus according to claim 1 wherein said outer nozzle portion surrounds said inner nozzle portion.

3. The apparatus according to claim 2 wherein said outer nozzle portion distal end has an annular skin engagement surface for engaging said skin around a skin pore and forming an annular seal with said skin about the skin pore whereby the vacuum produced by said vacuum producing means at said nozzle will cause the skin surrounding the skin pore to deform and be drawn into said outer nozzle portion opening by said vacuum.

4. The apparatus according to claim 3 wherein said outer nozzle portion is spaced from said inner nozzle portion to define an annular space therebetween when both said outer nozzle distal end and said inner nozzle distal end are in contact with said skin.

5. The apparatus according to claim 2 wherein said inner nozzle portion distal end has an annular skin engagement surface for engaging said skin around a skin pore after said skin has been deformed and drawn into said outer nozzle portion by said vacuum, said inner nozzle portion distal end forming an annular seal with the skin deformed and drawn into said outer nozzle portion by said vacuum when both said outer nozzle distal end and said inner nozzle distal end are in contact with said skin, the annular seal formed between the skin and the annular skin engagement surface of said inner nozzle portion distal end being located within the confines of an annular seal formed between the skin and said outer nozzle portion distal end.

6. The apparatus according to claim 1 additionally comprising means defining an air flow pathway between said nozzle and said vacuum producing means.

7. The apparatus according to claim 6 wherein said means defining an air flow pathway comprises a flexible conduit.

8. The apparatus according to claim 1 additionally comprising filter means positioned between the inner nozzle portion distal end and said vacuum producing means for engagement by material removed from a skin pore by said apparatus to prevent said material from reaching said vacuum producing means.

9. The apparatus according to claim 1 wherein said inner nozzle portion is one of a plurality of interchangeable inner nozzle portions of differing sizes of configurations, each inner nozzle portion of said plurality of interchangeable inner nozzle portions being connectable to the remainder of said apparatus.

10. The apparatus according to claim 1 wherein said biasing means comprises a coil compression spring.

11. The apparatus according to claim 1 additionally comprising a housing surrounding said outer nozzle portion and said inner nozzle portion, said inner nozzle portion being substantially immobile relative to said housing when said apparatus is employed to remove material from a skin pore.

12. The apparatus according to claim 11 wherein both of said nozzle portions are selectively removable from said housing.

13. The apparatus according to claim 6 wherein said air flow pathway leads to said inner nozzle portion interior.

14. An apparatus for removing material from a skin pore, said apparatus comprising, in combination:

a nozzle for engaging the skin of an individual, said nozzle including an outer nozzle portion having an outer nozzle portion distal end defining an outer nozzle portion opening and having an annular skin engaging surface surrounding said outer nozzle portion opening, said nozzle additionally including an inner nozzle portion having an inner nozzle portion distal end defining an inner nozzle portion opening, said outer nozzle portion being movably mounted relative to said inner nozzle portion and movable between a first position wherein said inner nozzle portion distal end is spaced from and out of contact with skin engaged by said outer nozzle portion distal end and a second position wherein said outer nozzle portion is retracted relative to said inner nozzle portion and said inner nozzle portion distal end is in contact with skin engaged by said nozzle;

biasing means biasing said outer nozzle portion to said first position; and vacuum producing means for producing a vacuum at said nozzle for applying a vacuum to skin engaged by said outer nozzle portion and said inner nozzle portion of said nozzle for removing material from a pore of said skin, said outer nozzle portion defining an outer nozzle portion interior in communication with said outer nozzle portion opening and said inner nozzle portion defining an inner nozzle portion interior in communication with said inner nozzle portion opening, said inner nozzle portion being at least partially disposed in said outer nozzle portion interior, said outer nozzle portion surrounding said inner nozzle portion, said inner nozzle portion distal end having an annular skin engagement surface for engaging said skin around a skin pore after said skin has been deformed and drawn into said outer nozzle portion by said vacuum and said outer nozzle portion has been displaced from said first position to said second position, said inner nozzle portion distal end forming an annular seal with the skin deformed and drawn into said outer nozzle portion by said vacuum, the annular seal formed between the skin and the annular skin engagement surface of said inner nozzle portion distal end being located within the confines of the annular seal formed between the skin and the annular skin engagement surface of said outer nozzle portion distal end.

* * * * *